United States Patent [19]

Yamada et al.

[11] Patent Number: 4,994,398
[45] Date of Patent: Feb. 19, 1991

[54] ASSISTANT COMBUSTION AGENT FOR USE IN HIGH-FREQUENCY COMBUSTION FURNACE

[75] Inventors: Takeshi Yamada; Mitsuhiko Chishiro; Katsuya Tsuji, all of Kyoto, Japan

[73] Assignee: Horiba, Ltd., Kyoto, Japan

[21] Appl. No.: 157,853

[22] Filed: Feb. 18, 1988

[30] Foreign Application Priority Data

Feb. 20, 1987 [JP] Japan .................................. 62-24436

[51] Int. Cl.$^5$ ...................... G01N 31/10; G01N 31/12
[52] U.S. Cl. ...................................... 436/166; 419/66; 419/68; 422/78; 436/73; 436/159; 436/160
[58] Field of Search ................. 436/73, 159, 160, 166; 422/78; 419/66, 68

[56] References Cited

U.S. PATENT DOCUMENTS

| | | | |
|---|---|---|---|
| 3,464,795 | 9/1969 | Schmitt et al. | 436/159 |
| 4,400,354 | 8/1983 | Culmo | 436/159 X |
| 4,806,489 | 2/1989 | Beach | 436/73 X |

FOREIGN PATENT DOCUMENTS 59-191671 12/1984 Japan .

Primary Examiner—Robert J. Warden
Assistant Examiner—Jill Johnston
Attorney, Agent, or Firm—Price, Gess & Ubell

[57] ABSTRACT

An assistant combustion agent for use in a high-frequency combustion furnace is characterized by a blending together of tungsten powder and tin powder. The blended mixture is then molded into a form and a plurality of the molded forms are added to a sample in the furnace. The ratio of tungsten powder to tin powder is between about 80:20 to 60:40.

7 Claims, 2 Drawing Sheets

ASSISTANT COMBUSTION AGENT FOR USE IN HIGH-FREQUENCY COMBUSTION FURNACE

BACKGROUND OF THE INVENTION

1. Field of the Invention

The present invention generally relates to an assistant combustion agent used in a high-frequency combustion furnace for elemental analysis of carbon, sulfur or the like which are contained in a steel and iron sample, and a nonferrous metal sample.

2. Description of Related Art

A prior method of elemental analysis with a high-frequency combustion furnace has utilized a crucible made of ceramics housing a weighed amount of a steel and iron sample and a nonferrous metal sample. The samples are then heated by passing a high-frequency current through the samples and blowing oxygen gas at the same time to burn the samples. Subsequently, the combustion gas which is formed is transported by a carrier gas into an analyzer where the combustion gas is analyzed.

However, in the above described combustion, the samples cannot provide a sufficiently high combustion temperature (1,600° to 1,800° C.) and so carbon and sulfur are insufficiently extracted. Thus, in general, tungsten and tin have been used as an assistant combustion agent.

But, even the above described method using an assistant combustion agent has exhibited disadvantages. Tungsten is advantageous in that a specific resistance heat generated by the high-frequency current and a combustion heat are increased to promote an oxidation process. However, tungsten cannot cover all the sample where the sample is formed in a block-like shape or where the weight of the sample is relatively large. As a result, only portions of the sample brought into contact with tungsten are heated until high temperatures to burn out, whereby producing metallic films A, A and cavities B, B, as disclosed in FIG. 4, and the supply of the oxygen gas to these cavities B, B becomes insufficient to make the extraction of carbon and sulfur complete.

On the other hand, tin has exhibited a basic advantage in that a melting point and viscosity of the sample are reduced to satisfactorily bring the oxygen gas into contact all over the sample, whereby a satisfactory extraction can be achieved. However, a disadvantage has occurred in that tin cannot effect the generation of heat as does tungsten, whereby the analysis becomes difficult.

Accordingly, in order to satisfactorily burn the sample and carry out the complete extraction even in the case where the sample is formed in a block-like shape, or in the case where the weight of the sample is relatively large, a mixture comprising tungsten and tin at an appointed ratio has been used as an assistant combustion agent.

In the preparation of the mixture comprising tungsten and tin, those two elements have been separately weighed in the crucible and their mixture has been used as the assistant combustion agent. The assistant combustion agent has been put in the crucible together with the sample. However, the mixture has been inferior in uniformity, and the mixing process has taken much time, whereby the efficiency of the analytical operation itself is lowered.

To overcome at least some of the above problems, tungsten has been coated with tin or tin coated with tungsten to integrate tungsten with tin, as disclosed in Japanese Patent Laid-Open No. Sho 59-191671 and applied for by Horiba, Ltd. That method seeks to make the time required for mixing tungsten with tin in the analytical operation unnecessary and to carry out the analytical operation efficiently.

However, since tin is coated on a circumference of tungsten by immersing granular tungsten (having a particle diameter of, for example, 1.0 mm) in molten tin, when tungsten is integrated with tin by coating, a disadvantage has occurred in that a mixing ratio of tungsten and tin in the assistant combustion agent is apt to fluctuate.

SUMMARY OF THE INVENTION

The present invention was achieved in view of the above described matters and disadvantages. It is an object of the present utility model to provide a uniform assistant combustion agent formed of a mixture comprising tungsten and tin at an appointed ratio.

In order to achieve the above described objects, an assistant combustion agent for use in a high-frequency combustion furnace according to the present invention is characterized by mixing tungsten powders and tin powders in an appointed ratio and the resulting mixture is molded in an appointed form.

With the above described characteristic construction, the integrated assembly formed of the mixture comprising tungsten and tin at an appointed ratio is previously prepared and superior in uniformity. For the sure combustion of the sample and the desired extraction it thus becomes necessary to only put an appointed quantity of assistant combustion agent in the crucible in accordance with the quantity or size of the sample in the analytical operation.

DESCRIPTION OF THE PREFERRED EMBODIMENTS

One preferred embodiment of the present invention is below described with reference to the drawings.

Figure 1:
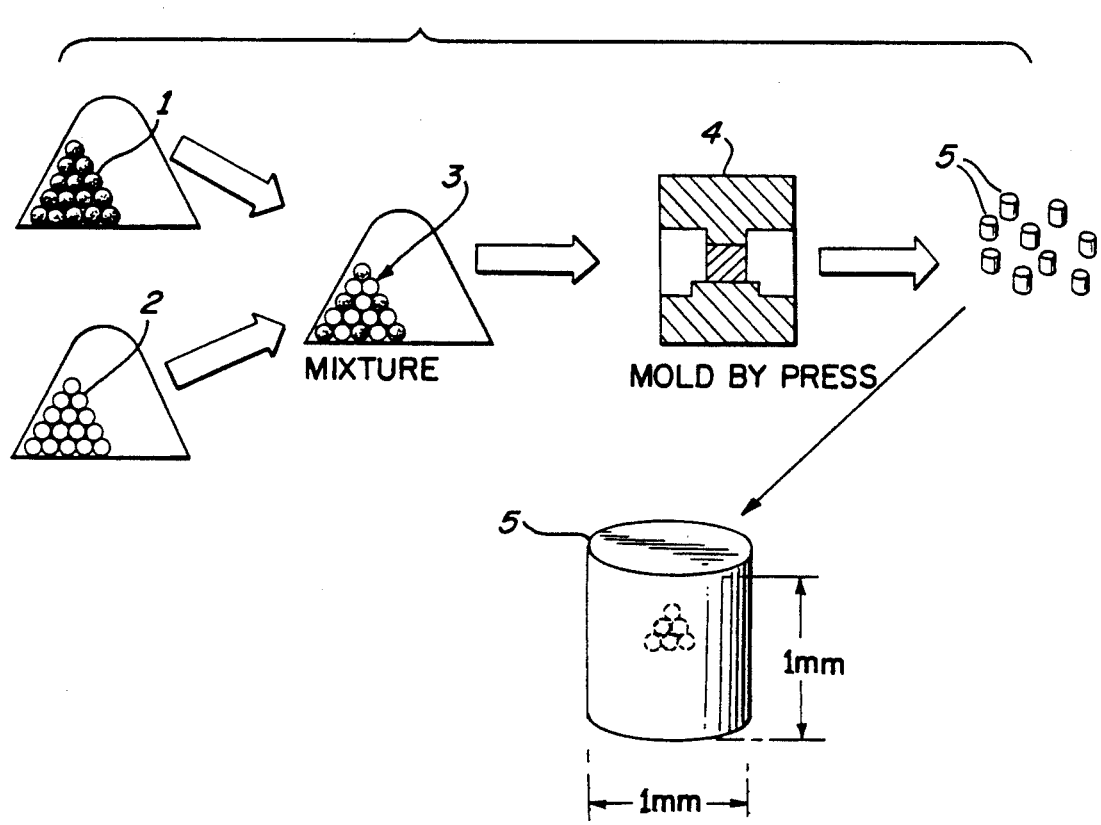
FIG. 1 is a diagram that explains the manufacturing of an assistant combustion agent according to the present invention.

FIG. 1 is a process chart of the manufacture of an assistant combustion agent according to the present invention. Referring now to FIG. 1, reference numeral 1 designates a tungsten powder of high purity (having a diameter of, for example, 70 microns) and reference numeral 2 designates a tin powder of high purity (having a diameter of, for example, 50 to 70 microns). These powders are separately weighed and then sufficiently blended so as to obtain a mixture comprising tungsten powders and tin powders at a ratio of, for example, 80:20.

Subsequently, a mixture 3 obtained by sufficient blending in the above described manner is molded in, for example, a press 4 to form a columnar assistant combustion agent 5 having a diameter of, for example, 1 mm and a height of, for example, 1 mm. The assistant combustion agent 5 formed in such a manner is used in a combustion in a high-frequency heating furnace shown in FIG. 2.

Figure 2:
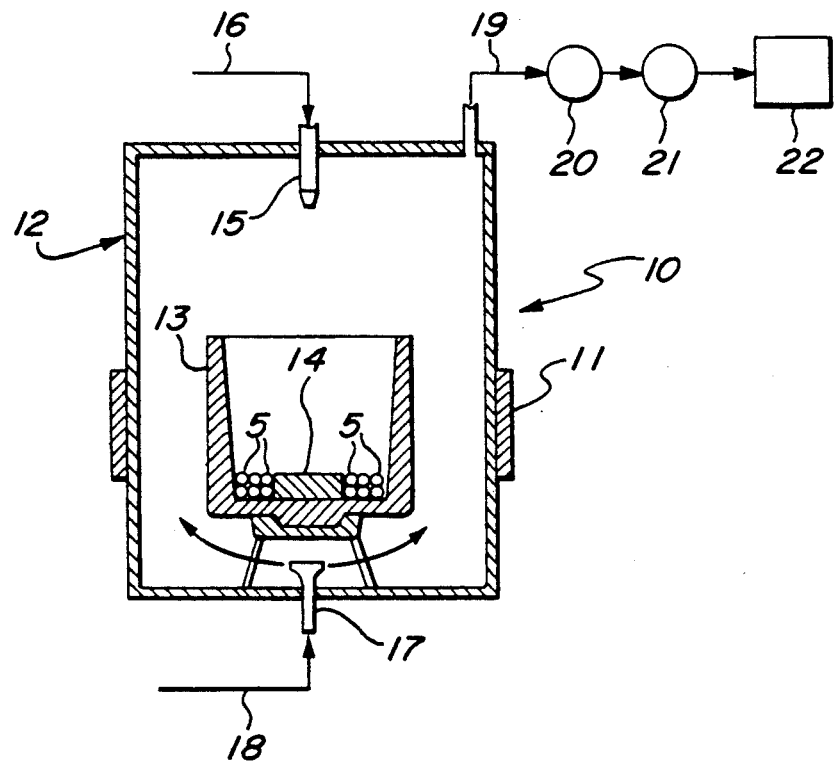
FIG. 2 is a view showing one example of a high-frequency heating furnace.

Referring now to FIG. 2, reference numeral 10 designates a high-frequency heating furnace comprising a closed furnace 12 provided with a high-frequency current-developing device 11. A crucible 13 is put in the closed furnace 12 and a sample 14 (although this is shown in a block-like shape here, this may be used in the form of stock or powder) and said assistant combustion agent 5 are housed in this crucible 13 at the same time in an appointed quantity. Reference numeral 15 designates a blowing nozzle suspended at the top of the closed furnace 12 toward an inside of the crucible 13 for blowing oxygen gas against the sample 14 and the assistant combustion agent 5 within the crucible 13. Reference numeral 16 designates an oxygen gas supply passage. Reference numeral 17 designates a discharge nozzle provided at the bottom of the closed furnace 12 for blowing out a carrier gas upward and carrying and extracting gases formed by the combustion of the sample 14 within the crucible 13. Reference numeral 18 designates a carrier gas passage. Reference numeral 19 designates a gas passage for taking out and supplying said formed gases to analyzers 20, 21. Reference numeral 22 designates an exhaust-gas treatment device.

Figure 3:
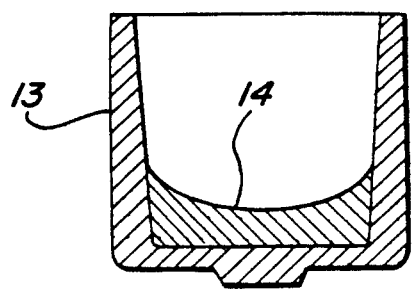
FIG. 3 is a diagram that explains a phenomenon that occurs when the assistant combustion agent according to the present invention is used.
Figure 4:
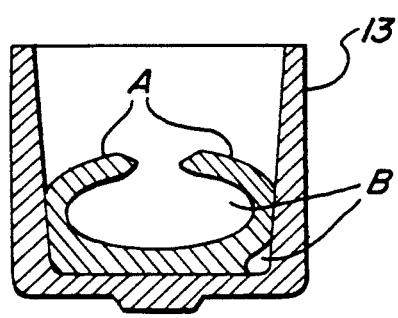
FIG. 4 is a diagram that explains a phenomenon that occurs when merely tungsten is used as an assistant combustion agent.

The sample 14 was burnt using the assistant combustion agent 5 in the high-frequency heating furnace 10 having the above described construction. It was obvious that the sample 14 was molten under the condition that a fluidity was high and gases were satisfactorily extracted from a surface of the sample 14, as shown in FIG. 3

In addition, it is not always necessary to form the assistant combustion agent 5 in a columnar shape as above described. It may be used in, for example, a spherical shape, cubical shape, and the like. And, as to a size of the assistant combustion agent 5, it is necessary only to have a size necessary for the generation of an eddy current when a high-frequency current is passed. For example, a diameter or one side of about 1 to 3 mm is preferable. If the assistant combustion agent 5 is too large in size, the combustion of the sample 14 is hindered.

In addition, a suitable mixing ratio of the tungsten powder 1 and the tin powder 2 is in a range of 80:20 to 60:40. If the tin powder 2 is too large in quantity, the quantity of dust generated is increased.

As above described, an assistant combustion agent for use in a high-frequency heating furnace according to the present invention is obtained by mixing tungsten powder and tin powder at an appointed ratio and molding the resulting mixture in an appointed shape, so that an integrated assembly formed of the mixture comprising tungsten powder and tin powder at the appointed ratio is previously obtained and the mixture is superior in uniformity. Accordingly, in an analytical operation it is necessary for surely achieving the combustion of the sample to only put the appointed quantity of the assistant combustion agent in the crucible in accordance with a quantity or size of the sample, whereby the desired extraction can be achieved. And, according to the present invention, in the analysis it is not required to separately weigh tungsten and tin, whereby the analysis can be efficiently achieved. In particular, the present invention exhibits a great effect in promotion of the automation of this type analysis.

What is claimed is:

1. An assistant combustion agent for use in a high-frequency combustion furnace, comprising:
   tungsten powder; and
   tin powder mixed with the tungsten powder at an appointed ratio to provide a resulting mixture that is molded in an appointed form to provide a homogeneous structure of a mixed blend of tungsten and tin powder.

2. An assistant combustion agent as set forth in claim 1, in which said appointed ratio of tungsten powder to tin powder is in a range of between about 80:20 to 60:40 by weight.

3. An assistant combustion agent as set forth in claim 1, in which said appointed form is one of a columnar form, spherical form, and a cubic form.

4. An improved assistant combustion agent of the type containing tungsten and tin, wherein the improvement consists of:
   a molded mixture of only tungsten powder and tin powder that have been blended together to form a homogeneous mixture and press molded to form a composite structure, the tungsten powder and the tin powder having been blended in a ratio of between about 80:20 to 60:40 by weight, and the respective diameter size of the tungsten and tin powder being in the range of 70 microns.

5. The combustion agent of claim 4 wherein the composite structure is a pellet of about 1 to 3 mm in dimensional size.

6. An assistant combustion agent for use in a high-frequency combustion furnace, comprising:
   tungsten powder; and
   tin powder mixed with the tungsten powder at a ratio of tungsten powder to tin powder in a range of between about 80:20 to 60:40 by weight, the resulting mixture is molded in an appointed form to provide a composite structure of a mixed blend of tungsten and tin powder with the size of the respective tungsten and tin powder being in a diametrical range of 70 microns.

7. The assistant combustion agent as set forth in claim 6 wherein the size of the appointed form is in the range of 1 to 3 mm in length and thickness.

* * * * *